(12) United States Patent
Zhao et al.

(10) Patent No.: US 10,500,325 B2
(45) Date of Patent: Dec. 10, 2019

(54) WEARABLE FILTRATING ARTIFICIAL KIDNEY DEVICE

(71) Applicant: SICHUAN UNIVERSITY, Sichuan (CN)

(72) Inventors: Changsheng Zhao, Sichuan (CN); Baihai Su, Sichuan (CN); Weifeng Zhao, Sichuan (CN); Shudong Sun, Sichuan (CN); Chen Wang, Sichuan (CN); Zhenqiang Shi, Sichuan (CN); Qiang Liu, Sichuan (CN); Xiaohua Zhang, Sichuan (CN); Ping Fu, Sichuan (CN); Jianhui Zhou, Sichuan (CN)

( * ) Notice: Subject to any disclaimer, the term of this patent is extended or adjusted under 35 U.S.C. 154(b) by 371 days.

(21) Appl. No.: 15/521,621

(22) PCT Filed: Sep. 23, 2016

(86) PCT No.: PCT/CN2016/099811
§ 371 (c)(1),
(2) Date: Apr. 25, 2017

(87) PCT Pub. No.: WO2018/053779
PCT Pub. Date: Mar. 29, 2018

(65) Prior Publication Data
US 2019/0099536 A1    Apr. 4, 2019

(51) Int. Cl.
*A61M 1/16* (2006.01)
*A61M 1/36* (2006.01)
*A61M 1/30* (2006.01)

(52) U.S. Cl.
CPC ........ *A61M 1/1621* (2014.02); *A61M 1/1654* (2013.01); *A61M 1/30* (2013.01);
(Continued)

(58) Field of Classification Search
CPC .... A61M 1/1621; A61M 1/1654; A61M 1/30; A61M 1/34; A61M 1/3672;
(Continued)

(56) References Cited

U.S. PATENT DOCUMENTS

| 2002/0060180 A1* | 5/2002 | Sugisaki | A61M 1/16 210/263 |
| 2008/0217245 A1* | 9/2008 | Rambod | A61M 1/16 210/637 |
| 2014/0217027 A1* | 8/2014 | Meyer | A61M 1/1601 210/646 |

* cited by examiner

*Primary Examiner* — Dirk R Bass
(74) *Attorney, Agent, or Firm* — W&K IP

(57) ABSTRACT

A wearable filtrating artificial kidney device, comprising a transfusion inlet (2), a blood pump (3), an arterial pressure detector (4), a blood filter (7), a venous pressure detector (8) and an air detector (9), wherein the transfusion inlet (2), the blood pump (3), the arterial pressure detector (4), a resin hemoperfusion apparatus (5), an active carbon hemoperfusion apparatus (6), the blood filter (7), the venous pressure detector (8) and the air detector (9) are connected sequentially; a liquid waste outlet of the blood filter (7) is connected with an ultrafiltration control pump (10). Glomerulus filtration can be simulated to achieve the goal of removing toxins and excessive moisture in the blood by virtue of ultrafiltration of the blood filter (7). A dialyzate and a complicated dialyzate circulating device are not used for the device, so that the volume and weight of the device can be reduced greatly, and the device can be worn conveniently. The device is simple in structure, easy in operation and low in cost.

3 Claims, 1 Drawing Sheet

(52) U.S. Cl.
CPC ... *A61M 1/3672* (2013.01); *A61M 2202/0413* (2013.01); *A61M 2209/088* (2013.01)

(58) Field of Classification Search
CPC ........ A61M 1/3679; A61M 2202/0413; A61M 2205/3355; A61M 2209/088
See application file for complete search history.

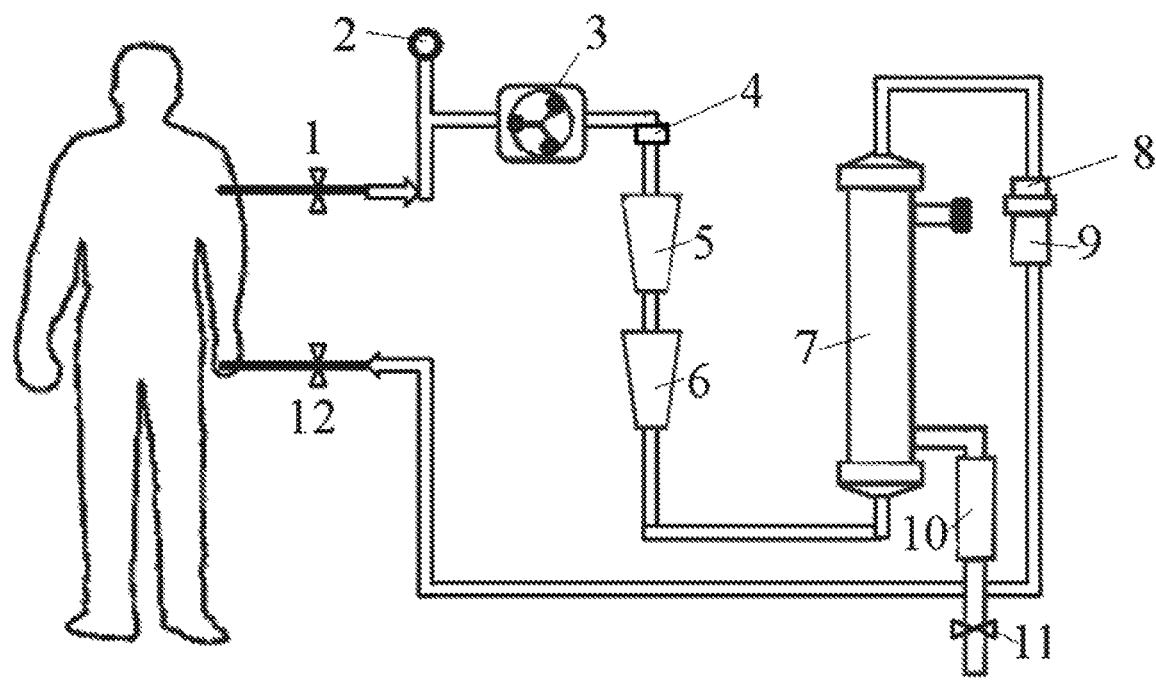

WEARABLE FILTRATING ARTIFICIAL KIDNEY DEVICE

BACKGROUND OF THE INVENTION

The present invention relates to biomedical equipment, and particularly relates to a wearable filtrating artificial kidney device.

An artificial kidney is a device for replacing the kidney function, which is mainly used for treating kidney failure and uremia. The device is used for taking venous blood out of the body and then removing excessive nitrogen-containing compounds, metabolic products or medicines in vivo by virtue of dialysis, filtration, absorption and membrane separation, and finally introducing the purified blood in vivo after the electrolyte balance is regulated.

The current artificial kidney device mainly involves hematodialysis type or hemoperfusion type. F-P Hoving et al. provided an artificial kidney for gradual and at least semi-continuous blood processing (CN201210350296). In the artificial kidney, anticoagulation is realized first; and then blood cells, as well as the large and moderate molecular weights of molecules (like protein) are preliminarily separated from plasma and then transfused to the blood again; and finally, accumulated substances and toxic substances are further removed from blood, plasma or plasma water by shunting excessive plasma water and removing specific electrolyte and wastes, in order to regulate water-salt balance, wherein the purified or partially purified plasma and plasma water are transfused to blood vessels in the body. Peng Luomin et al. invented a multi-functional portable artificial kidney (CN200610070809), with which the dialysate supply system can be simplified, and the capacity can be monitored precisely, so that the device can be applied flexibly independent of acetic acid for dialysis and water resource. Zhao Zuoning et al. invented a movable artificial kidney (CN03214805), which involves an artificial kidney host. A water supply system connected with the artificial kidney host consists of a dialyzate storage tank, a constant pressure water pump and a water supply pipeline. A-D Belz et al. invented a portable artificial kidney without auxiliary equipment (CN93104127), where the size and shape result in light weight and small size. It can be worn or attached to the body of a patient, without affecting the normal human physical activity. The artificial kidney has a plasma separating unit used for receiving the impure blood from the body, and then separating the prescribed amount of plasma, and finally transfusing the plasma in the separating part to the body again. The separated plasma passes through a chemical processing unit in which uric acid, creatinine, phosphate and ammonium ion are removed from the toxic plasma. The detoxified plasma is transmitted to a dewatering unit, and then sent back to a human circulation system again. In 2009, the research team, headed by Victor Gura from Mount Sinai Medical Center in Los Angeles and David Geffen from Ronald Reagan UCLA Medical Center, already displayed a conceptual wearable artificial kidney (WAK). The artificial kidney also belongs to miniaturized haemodialysis equipment with the weight of only 10 pounds (about 4.5 kg), so it can be carried on the waist of the patient. Moreover, a hemodialysis machine with the complete treatment function would enter the clinical test stage prior to the end of 2015. Besides, Dong Fan et al. provided a combined artificial kidney (CN201380037335), which saves dismounting a hemoperfusion apparatus during use.

The main idea provided by the present invention is to use a blood filter to remove toxins and excessive moisture in the blood depending on ultrafiltration when the dialyzate and a dialyzate circulating system are not used. As a result, miniaturization and wearable performance of the artificial kidney device can be realized to facilitate the activities of the patient suffering from renal failure.

BRIEF SUMMARY OF THE INVENTION

The present invention aims to provide a new artificial kidney device capable of solving the above-mentioned problems, as well as the problems that an existing artificial kidney device is complicate in structure, high in volume, heavy in weight, and inconvenient to wear. By simulating the glomerulus filtration, the wearable artificial kidney is prepared by virtue of a blood filter, in order to realize a miniaturized wearable filtering artificial kidney device.

To achieve the above purpose, the technical scheme of the present invention is as follows: a wearable filtrating artificial kidney device, comprising a blood pipeline, wherein the blood pipeline is sequentially provided with a blood inlet switch, a transfusion inlet, a blood pump, an arterial pressure detector, a blood filter, a venous pressure detector, an air detector, and a blood outlet switch in a blood flowing direction;

the blood filter includes an inlet, an outlet and a liquid waste outlet, wherein the inlet and the outlet are connected with the blood pipeline, the liquid waste outlet is connected with a liquid waste pipeline on which an ultrafiltration control pump and a liquid waste switch are arranged, the arterial pressure detector and the venous pressure detector are respectively used for detecting pressure at an inlet end and an outlet end of the blood filter, and the air detector is used for detecting the amount of air in the returned blood.

Preferably, a resin hemoperfusion apparatus and an active carbon hemoperfusion apparatus are arranged between the arterial pressure detector and the blood filter.

Preferably, the active carbon hemoperfusion apparatus is internally provided with a membrane coated activated carbon adsorbent and/or an endotoxin adsorbent.

Preferably, the resin hemoperfusion apparatus is internally provided with a urease resin microsphere adsorbent and a $\beta 2$-microglobulin adsorbent.

Preferably, the arterial pressure detector, the venous pressure detector and the air detector are all provided with alarm units that give an alarm respectively while monitoring the data exceeds a preset threshold, and all detectors are connected with a display.

According to the present invention, the two ends of the blood pipeline are connected with blood vessels of the patient to form a closed loop together with the blood vessels. A blood inlet switch is arranged at a human blood outlet, while a blood outlet switch is arranged at a human blood inlet.

The transfusion inlet is actually an inlet, reserved for externally connecting with liquid, of the blood vessel. Heparin, diluent and other medical liquid medicines can be transfused for adjuvant treatment from the transfusion inlet as required.

The blood pump is used for controlling the blood flow rate in the blood pipeline.

The blood filter, with an anticoagulation function, is used for simulating the glomerular function to realize blood purification; an ultrafiltration control pump is connected with the blood filter to control the dehydrating amount.

The arterial pressure detector and the venous pressure detector are respectively used for detecting the pressure at an inlet end and an outlet end of the blood filter, and feeding back data to the controller when the pressure exceeds the scope of a threshold.

The air detector is used for detecting air needing to transfuse to the blood in the body of the patient from the blood filter, but feeding back data to the controller when the amount of air exceeds the scope of the threshold.

Recently, the hemoperfusion apparatus is mainly applied to acute or chronic drug poisoning, uremia middle molecular toxin adsorption, hepatopathy and pathogenic factor adsorption in the immunization field. Instead, the resin hemoperfusion apparatus applied by the present invention can absorb 2-microglobulin and decompose urea, and the active carbon hemoperfusion apparatus can absorb creatinine and has an acid-base balance function.

According to the device provided by the present invention, the blood flow velocity is 60-150 mL/min, the membrane area of the blood filter is 0.6-1.0 m2; the sorting coefficient of a blood filtration membrane to vitamin B12 is 0.9; the retention rate for albumin is not lower than 0.95; the ultrafiltration coefficient is not lower than 200 mL/kPa·h.

For resin hemoperfusion apparatus, the adsorption capacity for the 2-microglobulin is not less than 50 mg, and the decomposition rate for the urea is not less than 100 mg/h.

The active carbon hemoperfusion apparatus for creatinine has the adsorption capacity for the creatinine of not lower than 250 mg, and also has the acid-base balance.

Compared with the prior art, the present invention has the following advantages:

1. A dialyzate and a complicated dialyzate circulating device are not used for the device, so that the volume and weight of the device can be reduced greatly, and the device can be worn conveniently.

2. The problems that a large number of filtered solution cannot be drained and substitute liquid cannot be supplemented can be overcome in the prior art. The present invention innovatively provides a blood filtration+hemoperfusion model, which completes a part of theoretical dose with the aid of hemoperfusion, in order to form a blood filtration+hemoperfusion "hybrid" blood purification model; the blood filter is used for simulating the glomerular filtration to remove excessive moisture and parts of toxins in the blood; the hemoperfusion is used for removing β2-microglobulin and urea nitrogen, and remedying the deficiencies of pure blood filtration treatment effect.

3. The device provided by the present invention is simple in structure, easy in operation and low in cost, thereby easily realizing the large-scale industrialization.

BRIEF DESCRIPTION OF THE DRAWINGS

FIG. 1 shows the functional block diagram of the present invention.

In the FIGURE: 1. Blood inlet switch; 2. Transfusion inlet; 3. Blood pump; 4. Arterial pressure detector; 5. Resin hemoperfusion apparatus; 6. Active carbon hemoperfusion apparatus; 7. Blood filter, 8. Venous pressure detector; 9. Air detector; 10. Ultrafiltration control pump; 11. Liquid waste switch; 12. Blood outlet switch.

DETAILED DESCRIPTION OF THE INVENTION

The followings are further descriptions of the present invention with reference to the drawings:

Embodiment 1

Please refer to FIG. 1, a wearable filtrating artificial kidney device comprises a blood pipeline, wherein the blood pipeline is sequentially provided with a blood inlet switch 1, a transfusion inlet 2, a blood pump 3, an arterial pressure detector 4, a blood filter 7, a venous pressure detector 8, an air detector 9, and a blood outlet switch 12 in a blood flowing direction;

the blood filter 7 includes an inlet, an outlet and a liquid waste outlet, wherein the inlet and the outlet are connected with the blood pipeline, the liquid waste outlet is connected with a liquid waste pipeline on which an ultrafiltration control pump 10 and a liquid waste switch 11 are arranged, the arterial pressure detector 4 and the venous pressure detector 8 are respectively used for detecting pressure at an inlet end and an outlet end of the blood filter 7, and the air detector 9 is used for detecting the amount of bubbles in the returned blood.

In the embodiment: a resin hemoperfusion apparatus 5 and an active carbon hemoperfusion apparatus 6 are arranged between the arterial pressure detector 4 and the blood filter 7; the active carbon hemoperfusion apparatus 6 is internally provided with a membrane coated activated carbon adsorbent and/or an endotoxin adsorbent; the resin hemoperfusion apparatus 5 is internally provided with an urease resin microsphere adsorbent and a β2-microglobulin adsorbent; the arterial pressure detector 4, the venous pressure detector 8 and the bubble detector 9 are all provided with alarm units that give an alarm respectively while monitoring the data exceeds a preset threshold, and all detectors are connected with a display.

According to the present invention, all parts of the wearable filtrating artificial kidney device are miniaturized to facilitate wearing.

A blood inlet switch 1 and a blood outlet switch 12 are connected with blood vessels of a patient by the blood pipeline during treatment, and a diluent can be transfused into the transfusion inlet 2; the blood from the patent and the diluent input into the transfusion inlet 2 are delivered to an arterial pressure detector 4 for pressure detection by the blood pump 3, and then sequentially delivered to the resin hemoperfusion apparatus 5 and the active carbon hemoperfusion apparatus for blood purification; the purified blood is delivered to the blood filter 7 for further purification, and then delivered to a venous pressure detector 8 and an air detector 9 for detecting venous pressure and bubbles respectively, and finally returned to the blood of the patient after being detected to be safe.

Before treatment, the blood inlet switch 1 is closed, and heparin is transfused from the transfusion inlet 2 to realize heparinization of the blood pipeline, remove the bubbles in the blood pipeline, the resin hemoperfusion apparatus 5, the active carbon hemoperfusion apparatus 6 and the blood filter 7; the blood filter 7 and the ultrafiltration control pump 10 are started to filtrate normal saline on a liquid waste switch 11, and washing of the heparin saline is stopped after all bubbles are removed.

During treatment, the two ends of the blood pipelines are connected with the blood of the patient; the blood inlet switch 1 and the blood outlet switch 12 are opened so that a closed blood loop is constituted between the blood pipeline and the human body; the blood sequentially flows through a blood pump 3, the arterial pressure detector 4, the resin hemoperfusion apparatus 5, the active carbon hemoperfusion apparatus 6, the blood filter 7, the venous pressure detector 8 and the air detector 9 sequentially by virtue of the blood pipeline, and then purified by the resin hemoperfusion apparatus 5, the active carbon hemoperfusion apparatus 6 and the blood filter 7; the purified blood is returned to the patient in vivo after the liquid waste is removed from the liquid waste switch 11.

Upon treatment, the blood inlet switch 1 is closed, the normal saline is transfused from the transfusion inlet 2, and then is used for washing continuously and transfused to the patient in vivo; after the liquid waste is not discharged, the blood outlet switch 12 is turned off, and the blood filter 7 and the ultrafiltration control pump 10 are closed.

According to the device provided by the present invention, the blood flow velocity is 60-150 mL/min, the membrane area of the blood filter 7 is 0.6-1.0 m2; the sorting coefficient of a blood filtration membrane to vitamin B12 is 0.9; the retention rate for albumin is not lower than 0.95; the ultrafiltration coefficient is not lower than 200 mL/kPa·h.

The adsorption capacity of resin hemoperfusion apparatus 5 for the 2-microglobulin is not lower than 50 mg, and the decomposition rate for the urea is not lower than 100 mg/h.

The active carbon hemoperfusion apparatus 6 for creatinine has the adsorption capacity for the creatinine of not lower than 250 mg, and also has the acid-base balance.

The clinical pilot experimental results show that the dehydrating amount is 1-3 L, the total amount of 2-microglobulin is reduced by 30%, and the total amount of urea nitrogen is reduced by 30-35%.

What described above are only preferred embodiments of the present invention, which do not make any limitations to the technical scope of the present invention. Therefore, any minor amendments, equivalent alterations and modifications made for the above embodiments according to the technical essence of the present invention are still under the scope of the technical scheme provided by the present invention.

What is claimed is:

1. A wearable filtrating artificial kidney device, comprising a blood pipeline, wherein the blood pipeline is sequentially provided with a blood inlet switch (1), a transfusion inlet (2), a blood pump (3), an arterial pressure detector (4), a blood filter (7), a venous pressure detector (8), an air detector (9), and a blood outlet switch (12) in a blood flowing direction;

the blood filter (7) includes an inlet, an outlet and a liquid waste outlet, the inlet and the outlet are connected with the blood pipeline, the liquid waste outlet is connected with a liquid waste pipeline on which an ultrafiltration control pump (10) and a liquid waste switch (11) are arranged, the arterial pressure detector (4) and the venous pressure detector (8) are respectively used for detecting the pressure at an inlet end and an outlet end of the blood filter (7), and the air detector (9) is used for detecting the amount of bubbles in the returned blood;

a resin hemoperfusion apparatus (5) and an active carbon hemoperfusion apparatus (6) are arranged between the arterial pressure detector (4) and the blood filter (7);

the resin hemoperfusion apparatus (5) is internally provided with a urease resin microsphere adsorbent and a β2-microglobulin adsorbent.

2. The wearable flit rating artificial kidney device according to claim 1, wherein the active carbon hemoperfusion apparatus (6) is internally provided with a membrane coated activated carbon adsorbent and/or an endotoxin adsorbent.

3. The wearable filtrating artificial kidney device according to claim 1, wherein the arterial pressure detector (4), the venous pressure detector (8) and the air detector (9) are all provided with alarm units that give an alarm respectively while monitoring the data exceeds a preset threshold, and all detectors are connected with a display.

\* \* \* \* \*